(12) United States Patent
Ataollahi et al.

(10) Patent No.: US 9,675,781 B2
(45) Date of Patent: Jun. 13, 2017

(54) CONTINUUM MANIPULATOR

(75) Inventors: Asghar Ataollahi, London (GB);
Kaspar Althoefer, London (GB);
Tobias Richard Schaeffter, London
(GB); Kawaldeep Rhode, London (GB)

(73) Assignee: KINGS COLLEGE LONDON,
London (GB)

( * ) Notice: Subject to any disclaimer, the term of this patent is extended or adjusted under 35 U.S.C. 154(b) by 513 days.

(21) Appl. No.: 14/236,797

(22) PCT Filed: Aug. 1, 2012

(86) PCT No.: PCT/GB2012/051860
§ 371 (c)(1),
(2), (4) Date: Jun. 10, 2014

(87) PCT Pub. No.: WO2013/017875
PCT Pub. Date: Feb. 7, 2013

(65) Prior Publication Data
US 2014/0350462 A1    Nov. 27, 2014

(30) Foreign Application Priority Data

Aug. 4, 2011 (GB) .................. 1113532.4
Aug. 4, 2011 (GB) .................. 1113534.0
Aug. 4, 2011 (GB) .................. 1113536.5

(51) Int. Cl.
*A61B 1/00*     (2006.01)
*A61M 25/01*    (2006.01)
(Continued)

(52) U.S. Cl.
CPC ....... *A61M 25/0138* (2013.01); *A61B 1/0056* (2013.01); *A61B 1/0057* (2013.01);
(Continued)

(58) Field of Classification Search
CPC .......... A61M 25/0138; A61M 25/0147; A61M 2025/015; A61M 2025/0161;
(Continued)

(56) References Cited

U.S. PATENT DOCUMENTS 4,960,134 A * 10/1990 Webster, Jr. ...... A61M 25/0147
                                                   607/116
5,967,978 A * 10/1999 Littmann ............. A61B 5/0422
                                                   600/374
(Continued)

FOREIGN PATENT DOCUMENTS

CN        101703424 A    5/2010
EP        2123231 A1    11/2009
(Continued)

OTHER PUBLICATIONS

International Search Report mailed on Jan. 28, 2013, in application No. PCT/GB2012/051860.
(Continued)

*Primary Examiner* — Kevin C Sirmons
*Assistant Examiner* — William Carpenter
(74) *Attorney, Agent, or Firm* — Patterson + Sheridan, LLP

(57) ABSTRACT

Embodiments of the present invention provide a continuum manipulator that can be used, for example, as a steerable catheter tip. The manipulator of the embodiments comprises a plurality of segments arranged in a stack, which is then able to bend in a range of directions away from the long axis of the stack. In one embodiment the segments include a helical portion which winds in the direction of the long axis of the stack, and can thus bend away from the long axis in any direction. In some embodiments a carbon fiber rod is included as a backbone for the stack, to minimize hysteresis and improve repeatability of bending. In addition, in
(Continued)

embodiments of the invention tendon control channels are provided formed within the segments, through which tendon control wires extend to apply compression and/or bending forces to the stack.

15 Claims, 10 Drawing Sheets

(51) Int. Cl.
*A61B 1/005* (2006.01)
*A61B 1/313* (2006.01)
(52) U.S. Cl.
CPC ........ *A61B 1/00073* (2013.01); *A61B 1/3132* (2013.01); *A61M 25/0147* (2013.01)
(58) Field of Classification Search
CPC .......... A61M 25/0105; A61M 25/0013; A61M 25/0136; A61M 2025/0915
See application file for complete search history.

(56) References Cited

U.S. PATENT DOCUMENTS

| | | | | |
|---|---|---|---|---|
| 9,220,398 | B2* | 12/2015 | Woodley | A61B 1/0053 |
| 2002/0082584 | A1 | 6/2002 | Rosenman et al. | |
| 2004/0236316 | A1* | 11/2004 | Danitz | A61B 1/0055 |
| | | | | 606/1 |
| 2005/0273085 | A1* | 12/2005 | Hinman | A61B 1/0055 |
| | | | | 606/1 |
| 2006/0184106 | A1 | 8/2006 | McDaniel et al. | |
| 2008/0188928 | A1 | 8/2008 | Salahieh et al. | |
| 2009/0157048 | A1* | 6/2009 | Sutermeister | A61L 29/085 |
| | | | | 604/523 |
| 2009/0182268 | A1 | 7/2009 | Thielen et al. | |

FOREIGN PATENT DOCUMENTS

| | | | | |
|---|---|---|---|---|
| JP | 53-105493 | | 8/1978 | |
| JP | H05-184526 | A | 7/1993 | |
| JP | H08-141971 | A | 6/1996 | |
| JP | WO 2004105849 | A1 * | 12/2004 | ........ A61M 25/0013 |
| JP | 2007-502198 | A | 2/2007 | |
| JP | 2007-236976 | A | 9/2007 | |
| JP | EP 2123231 | A1 * | 11/2009 | .......... A61B 1/0052 |
| WO | 01/78825 | A2 | 10/2001 | |
| WO | 2004/105849 | A1 | 12/2004 | |
| WO | 2005/120326 | A2 | 12/2005 | |
| WO | 2007/057132 | A1 | 5/2007 | |
| WO | 2007/136829 | A1 | 11/2007 | |

OTHER PUBLICATIONS

Search Report issued in application No. GB1113534.0 dated Nov. 21, 2011.
Search Report issued in application No. GB1113536.5 dated Nov. 21, 2011.
Search Report issued in application No. GB1113532.4 dated Nov. 21, 2011.
CN Office Action dated Aug. 17, 2015 for Application No. 201280048365.0.
JP Office Action dated May 18, 2016 for Application No. JP2014-523390.

* cited by examiner

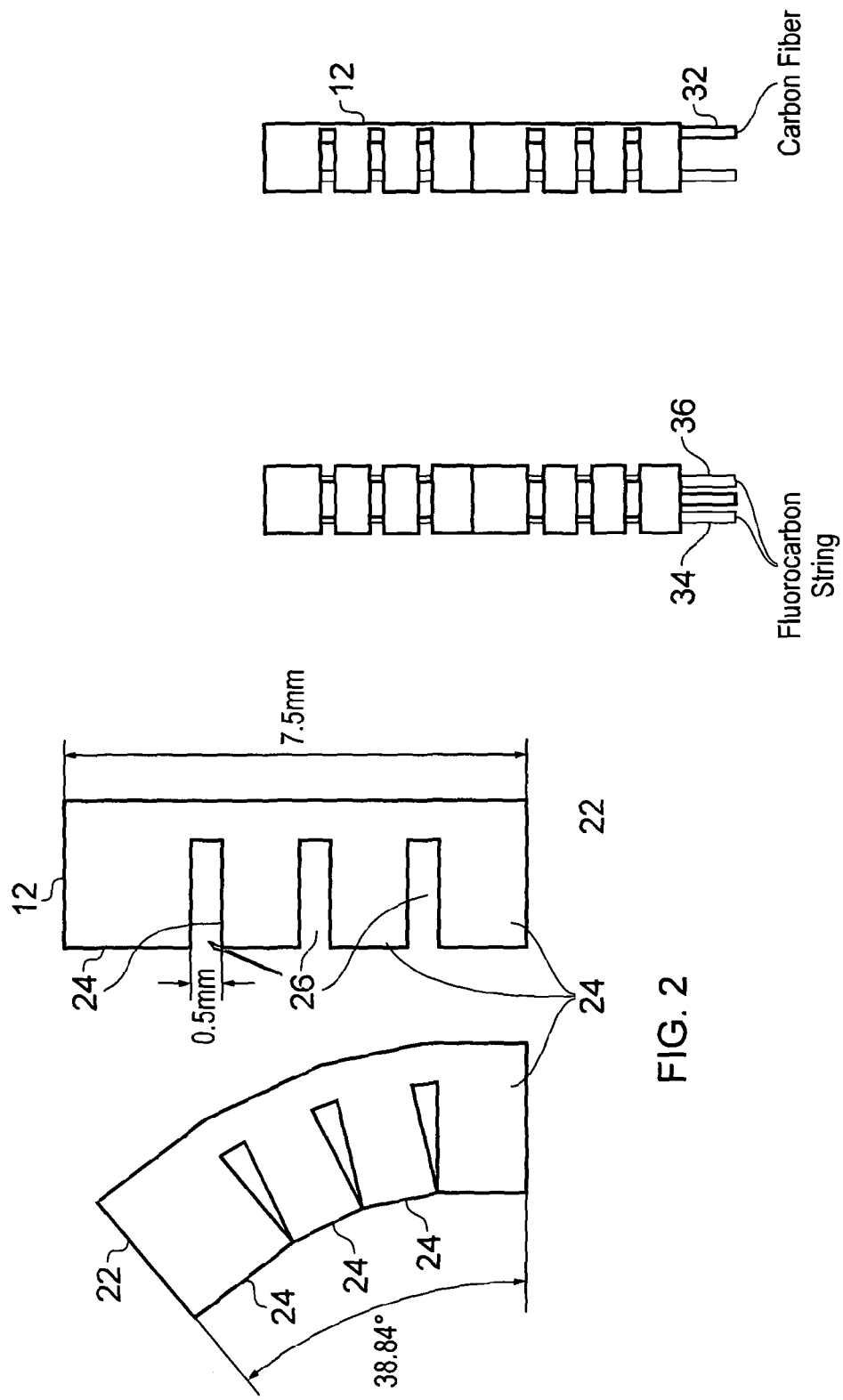

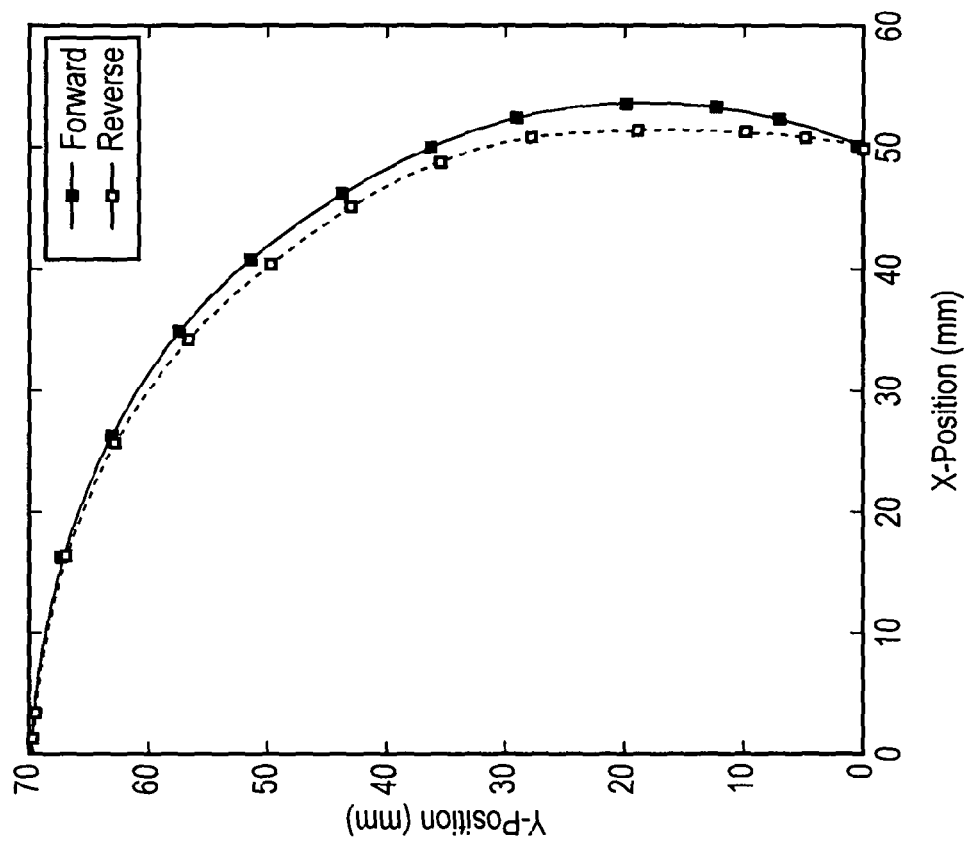
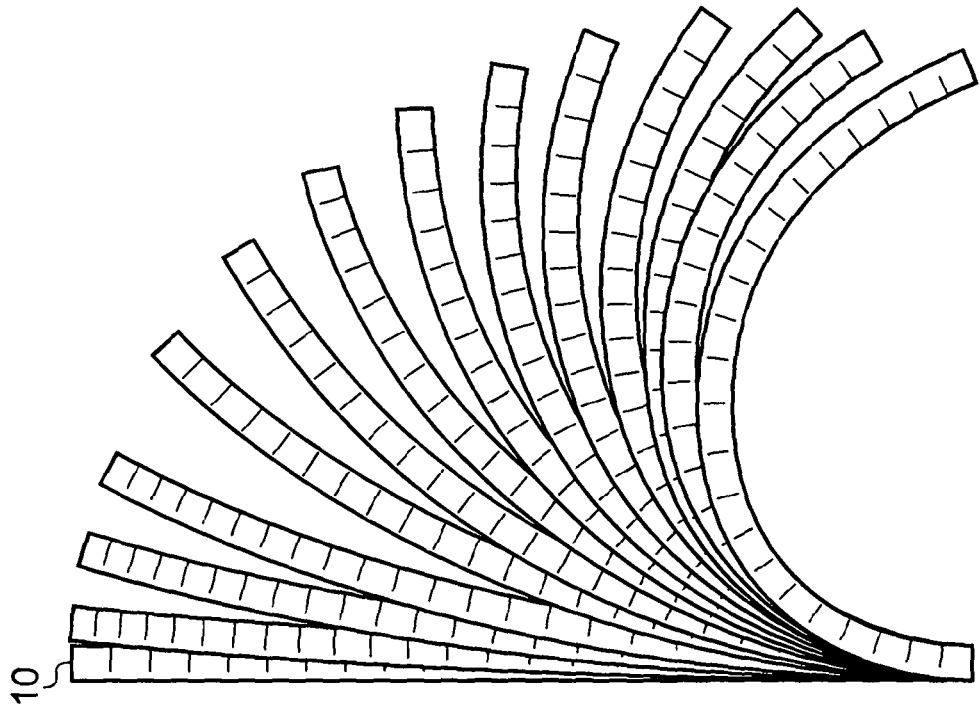
FIG. 6

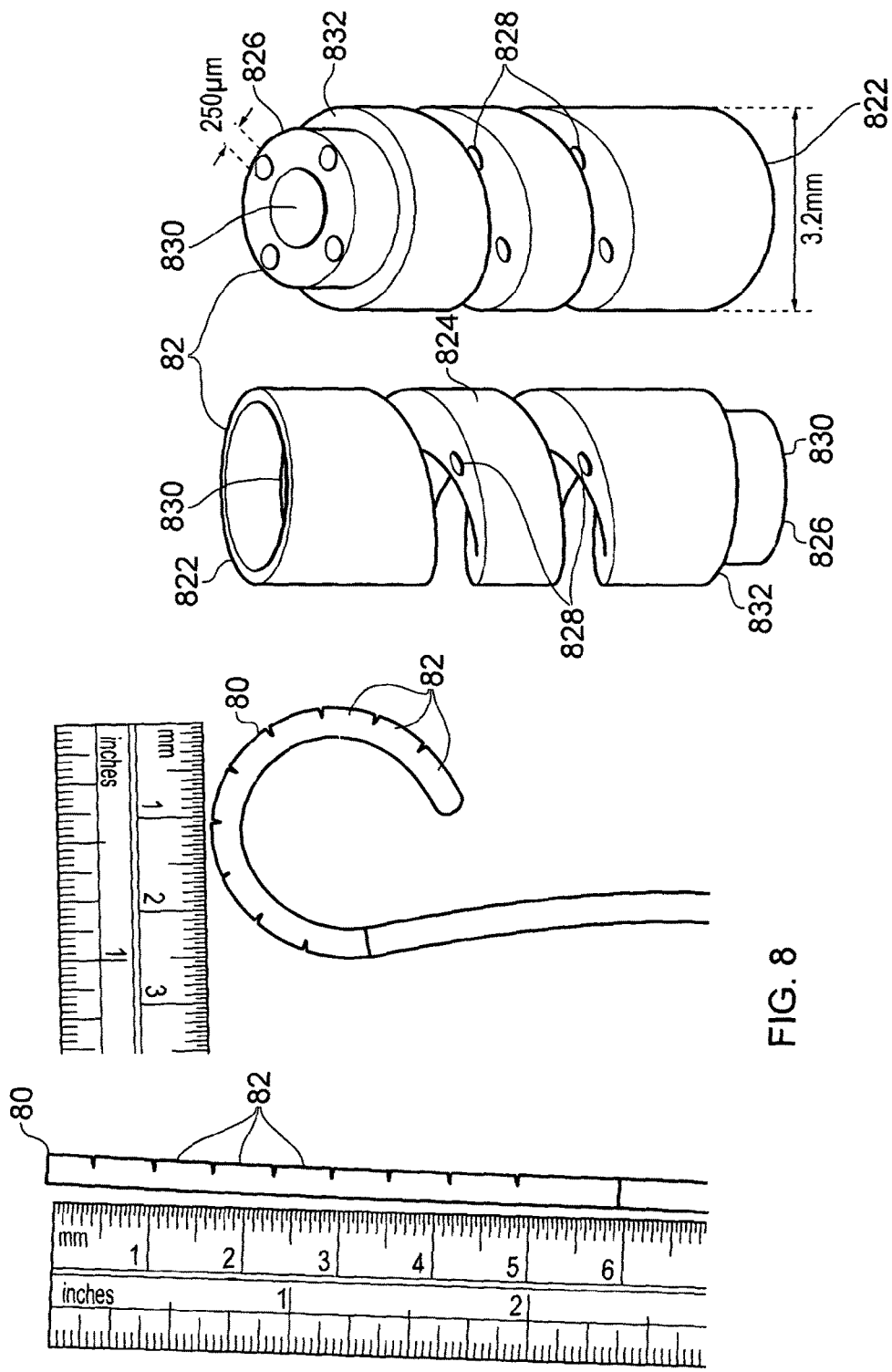

CONTINUUM MANIPULATOR

CROSS-REFERENCE TO RELATED APPLICATIONS

This application is a nation stage entry under 35 U.S.C. section 371 of PCT Application Serial No. PCT/GB2012/051860, filed on 1 Aug. 2012 and published as WO 2013/017875 on 7 Feb. 2013, which claims priority to GB provisional documents 1113534.0, 1113532.4, 1113536.5 all filed on 4 Aug. 2011.

TECHNICAL FIELD

The present invention relates to a continuum manipulator, and in one embodiment a continuum manipulator that is suitable for use as a steerable catheter tip usable in, for example, cardiac catheterisation procedures, endoscopic imaging, and medicine delivery, amongst other uses.

BACKGROUND TO THE INVENTION AND PRIOR ART

Cardiac catheterisation is a minimally invasive surgery (MIS) procedure performed using flexible, thin and long tubes called catheters. The catheter is inserted through a small incision into the femoral vein which leads to the heart, and the goal is usually to reach specific locations inside the body (e.g. the heart) and to perform examinations or treatments such as RF ablations. The main advantages of using catheters are the reduced trauma and shorter recovery time for the patient, but conventional catheters usually have limited degrees of freedom, as the catheter can typically only rotate and slide through the trocar port.

Most commercial catheters at present consist of a flexible plastic body and a manoeuvrable tip that is manipulated with preconfigured guide wires or tendons. Example prior art catheters are disclosed in Yi et al "Multiturn, Tension Stiffening Catheter Navigation System", *Robotics and Automation (ICRA)*, 2010 IEEE International Conference, pp 5570-5575, and P. Canagaratnam et al "Experience of Robotic Catheter Oblation in Humans Using a Novel Remotely Steerable Catheter Sheath", *Journal of Interventional Cardiac Electrophysiology*, Volume 21, pages 19 to 26, 2008, as well as in U.S. Pat. No. US RE40852, U.S. Pat. No. 4,586,923, and U.S. Pat. No. 6,980,843. In addition, imaging of conventional catheterisation procedures has typically been performed using x-ray fluoroscopy. However, this technique returns only 2D images with poor soft tissue contrast. To try and improve imaging during catheterisation procedures, and to reduce exposure to x-ray radiation, magnetic resonance imaging (MRI) techniques have started to be used but the use of magnetic resonance imaging requires that certain materials be used, and in particular non-ferrous and non-conductive materials.

To continue to improve and expand upon existing cardiac catheterisation techniques, there is a need for a catheter of increased steerability, and also manufactured from MR compatible materials.

SUMMARY OF THE INVENTION

Embodiments of the present invention provide a continuum manipulator that can be used, for example, as a steerable catheter tip. The manipulator of the embodiments comprises a plurality of segments arranged in a stack, which is then able to bend in a range of directions away from the long axis of the stack. In one embodiment the segments include a helical portion which winds in the direction of the long axis of the stack, and can thus bend away from the long axis in any direction. In another embodiment the segments include a backbone portion with cantilevered rings extending from the backbone portion, separated by bending gaps which allow the segment to bend in a range of directions away from the backbone portion so that the bending gap between the rings closes. In some embodiments an elastomeric rod such as, for example, a carbon fibre rod is included as a backbone for the stack, to minimise hysteresis and improve repeatability of bending. In addition, in embodiments of the invention tendon control channels are provided formed within the segments, through which tendon control wires extend to apply compression and/or bending forces to the stack. Having the control channels formed internally to the stack strengthens the stack and makes the stacked structure conform to the channel(s). In particular unwanted twisting of the tip of the stack can be prevented.

In view of the above, from one aspect there is provided a continuum manipulator comprising a plurality of segments arranged in a stack, the segments being deformable in a range of directions away from the long axis of the stack to allow the stack to bend in the range of directions away from the long axis thereof. The segments may further comprise a backbone channel running through each segment parallel to the long axis thereof and may be arranged in the stack with the respective backbone channels in alignment. An elastomeric rod may then be inserted into and run through the backbone channels of the segments. This provides significant advantages in allowing the stack to return to its original position after bending, and also to assume the same bent position for the same tendon displacement. That is, repeatability of bending is improved, and hysteresis in forwards and reverse bending is reduced.

In preferred embodiments of the invention the elastomeric rod is formed from a non-conductive material. This has additional advantages in some applications, such as a MR-guided catheterization application, in that the rod is then MRI compatible. In particularly preferred embodiments a carbon fibre rod is used, although other materials may also be used, such as high density polymers or the like, with suitable elastomeric properties.

From another aspect there is provided a continuum manipulator comprising a plurality of segments arranged in a stack, the segments being deformable in a range of directions away from the long axis of the stack to allow the stack to bend in the range of directions away from the long axis thereof. The segments may comprise at least one tendon guide channel formed internally therein substantially parallel to the long axis thereof, the stack of segments being arranged such that the tendon guide channels thereof are in alignment. A control tendon may then run through the guide channels and be affixed to at least one of the segments to allow a bending or compression force to be applied to the stack when the control tendon is activated.

Provision of such an internal tendon guide channel, internal to each segment, provides structural advantages to the continuum manipulator, as the control tendon within the guide channel forces the continuum stack to conform to the channel. This prevents unwanted twisting of the tip of the continuum stack, and improves torqueability of the tip i.e. the amount of torque that the tip can apply. In some applications this can be useful, for example in catheter ablation techniques.

From a further aspect there is provided a continuum manipulator comprising a plurality of segments arranged in a stack, the segments being deformable in a range of directions away from the long axis of the stack to allow the stack to bend in the range of directions away from the long axis thereof. At least one of the segments may comprise a helical portion wherein the wall of the segment extends helically around and in the direction of the long axis of the stack, the helical portion being able to deform in any direction away from the long axis. Such a structure provides significant advantages in allowing the stack to bend in any direction around 360° away from the long axis of the stack. In addition, the helical structure allows the segments to be compressed, by pulling all control tendons equally together, which increases the stiffness of the stack along its length. Being able to control the stiffness of the stack can be important in some applications.

In some embodiments the segments further comprise a lumen channel formed therein and extending parallel to the long axis thereof, the segments being arranged in the stack in alignment to provide a lumen channel running through the stack. The provision of a lumen channel allows other instruments or wires to extend along the stack.

In one embodiment provided with helical portions in a segment, the segment with the helical portion may further comprise a mating projection, and a mating ring. The mating projection is preferably located at an opposite end of the segment from the mating ring, the mating ring and mating projection being respectively sized such that the mating projection of one such segment is received within the mating ring of another such segment when such segments are arranged in the stack. With such an arrangement the different segments may be easily and reliably stacked one on top of each other to provide the continuum.

In one embodiment the segments comprise at least three, and preferably four, tendon guide channels formed therein substantially parallel to the long axis thereof. The manipulator also further includes respective control tendons running through the guide channels and affixed to at least one of the segments to allow a bending or compression force to be applied to the stack when one or more of the control tendons are activated, for example by having a force applied thereto. When used with the segments provided with the helical portions, three or four (or more) control tendons substantially equiangularly spaced around the circumference of the segments allows for control of the stack to cause the stack to bend in any direction away from the long axis of the stack.

In a preferred embodiment a majority of segments in the stack have helical portions. This provides for improved bending in any direction.

In one embodiment, a plurality of segments in the stack have helical portions, and a first subset of one or more segments of the plurality of segments have helical portions that wind in a clockwise direction. In addition, a second subset of one or more segments of the plurality of segments have helical portions that wind in a counter-clockwise direction. With such an arrangement unwanted twisting of the stack when a compression or bending force is applied via the control tendons can be compensated. In this respect, in one particularly preferred embodiment there are substantially equal numbers of segments in the stack with helical portions that wind clockwise and counter-clockwise, so that the net twisting experienced is almost all compensated.

In one embodiment at least some of the segments further comprise a twist control tendon channel, the twist control tendon channel being formed within a segment from a plurality of twist control channels that extend parallel to the long axis of the segment but only along a respective part of the length of the segment. The channels are laterally offset from one another, and a twist control tendon runs through the twist control channels, such that when a force is applied to the twist control tendon the twist control channels are pulled into alignment, thereby at least partially rotating at least part of the segment. Such an arrangement allows for controlled twisting of the stack, in addition or alternatively to controlled bending or compression.

In another embodiment the segments comprise a backbone portion containing the backbone channel, at least some of the segments further comprising a plurality of cantilevered rings extending from the backbone portion in the same direction, the rings being spaced along the backbone portion so as to have a bending gap therebetween. the provision of the bending gaps allows the segments to bend in a range of directions away from the backbone portion, to the extent allowed by the gaps. Hence, a maximum degree of bend can be built into the stack.

In this embodiment the at least two guide channels are formed in the walls of the rings, the range of angle of bending of the stack away from the long axis thereof being dependent on the location of the two guide channels with respect to the backbone channel, the movement range being less than 180°.

In one preferred embodiment the manipulator is a steerable catheter tip. In this embodiment the diameter of the stack is in the range 0.5 mm to 3 mm, and the length of each segment is in the range 1-100 mm.

The catheter tip is preferably made of magnetic resonance compatible materials, such as for example acrylate polymer. The control tendons may be formed from fluorocarbon string because of MR-compatibility, or of any other MR-compatible materials. For example, in other embodiments Nitinol string may be used.

BRIEF DESCRIPTION OF THE DRAWINGS

Further features and advantages of the present invention will become apparent from the following description of embodiments thereof, presented by way of example only, and wherein like reference numerals refer to like parts, and wherein:

FIG. 2 is a drawing illustrating a segment of the continuum manipulator of the first embodiment;

FIG. 3 is a pair of drawings illustrating the arrangement of plural segments making up part of the continuum manipulator of the first embodiment;

FIG. 6 is a series of overlapping photographs, and an accompanying graph of continuum manipulator position as the manipulator is actuated in forward and reverse direction to evaluate the hysteresis effect;

FIG. 8 is a pair of photographs illustrating a continuum manipulator arrangement of a second embodiment of the present invention;

FIG. 9 is a pair of drawings illustrating a segment of the continuum manipulator of the second embodiment;

DESCRIPTION OF THE PREFERRED EMBODIMENTS

A first embodiment of the present invention will now be described with respect to FIGS. 1 to 7.

Figure 1:
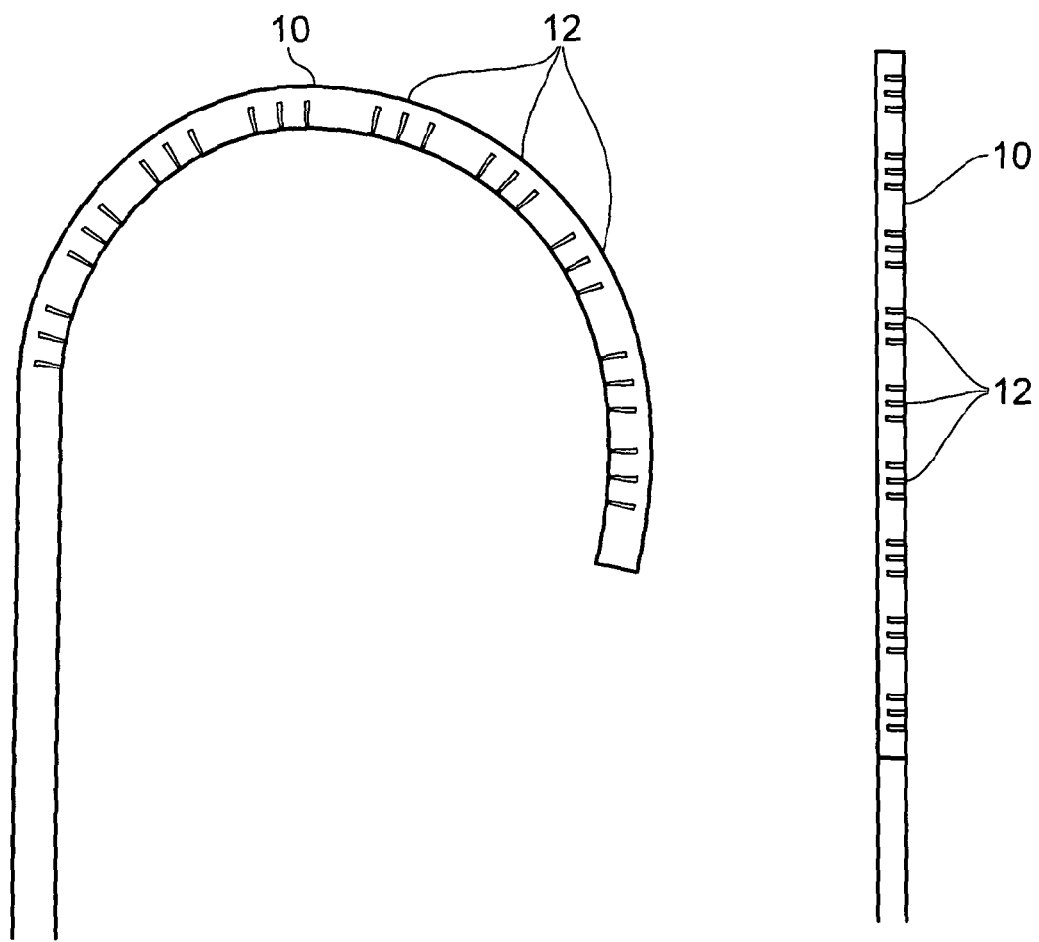
FIG. 1 is photograph of a multi-segment continuum manipulator according to a first embodiment of the invention.

The first embodiment of the present invention provides a continuum manipulator in the form of a steerable catheter tip 10, as shown in FIG. 1. The steerable catheter tip 10 is shown in the left hand photograph of FIG. 1 in a bent configuration, and in the right hand photograph in an unbent configuration. The steerable catheter tip 10 is formed from nine individual and interconnecting segments 12, which are effectively stacked one on top of the other along the long axis of the catheter tip to form a continuum structure. The number of segments may vary depending on application to enlarge or shorten the steerable length. Each segment 12 contains integral tendon channels through which steering or guide tendons of the catheter pass, as well as a backbone channel for a carbon fibre backbone, as will be described later. In operation, the steering tendons can be manipulated either by hand, or by robot, to cause the steerable catheter tip to bend, as shown in the left hand photograph of FIG. 1 thus providing a first degree of freedom, and also to adjust the position of the tip of the catheter sideways in either direction. In the present embodiment this sideways movement may be up to, for example, 22.5 degrees to either side. This sideways movement represents a second degree of freedom of the catheter tip.

FIG. 2 illustrates the arrangement of each segment 12. In particular, each segment 12 comprises a backbone portion 22 extending along the long axis of the segment, at one side of the segment. Extending outwards cantilevered to the side of the backbone portion are ring structures 24, which are separated from each other, other than where they join the backbone portion, by gaps 26. As will be seen, in the preferred embodiment each segment 12 is 7.5 mm long, with each gap 26 being 0.5 mm wide. This allows each segment to deflect by 38.84 degrees in total, in theory.

Figure 4:
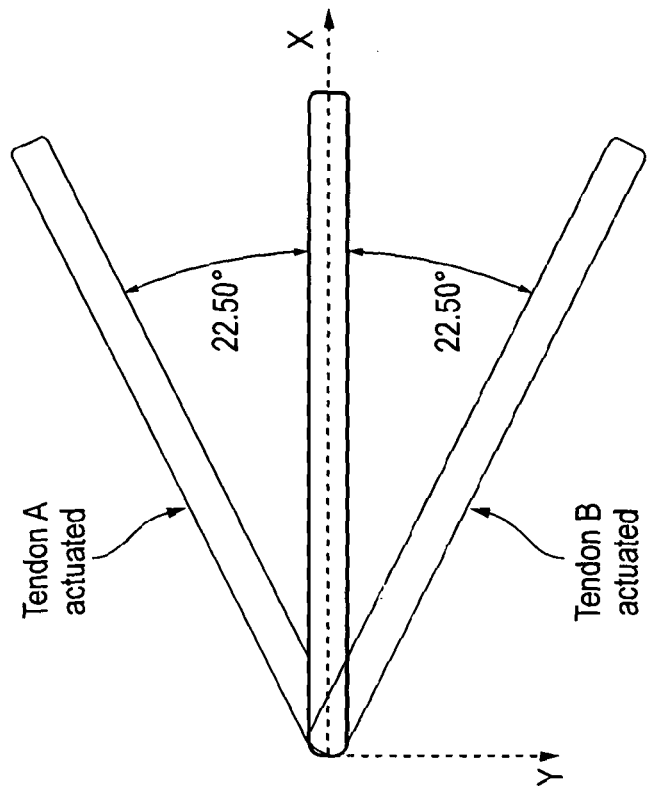
FIG. 4 is a cross-section of a segment of the continuum manipulator of the first embodiment.
Figure 5:
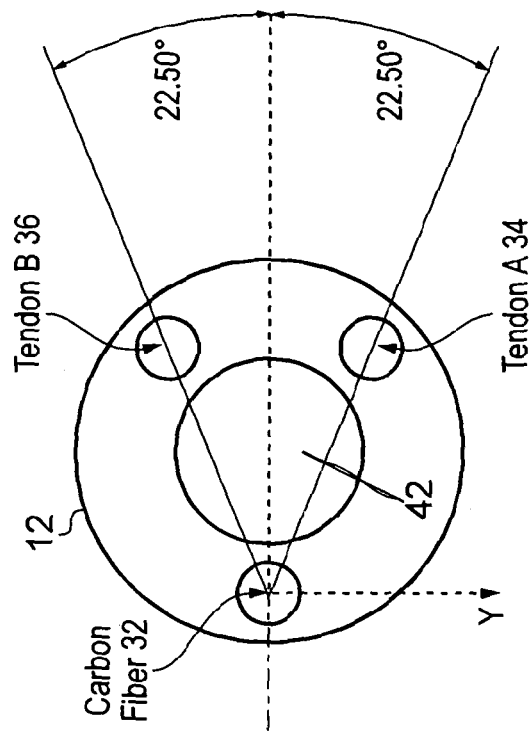
FIG. 5 is a diagram illustrating the range of movement of the continuum manipulator of the first embodiment.

Please note that each segment is essentially a tubular structure formed from the cantilevered ring structures 24, cantilevered outwards from the backbone portion 22. The outer diameter of the tubular structure in the present embodiment is 2.4 mm, with an inside lumen formed from the ring structures of an inner diameter of, for example, 1.3 mm. In other embodiments the outer diameter may be between 2.3 mm and 3 mm, and the inside lumen should have a minimum diameter of approximately 1 mm. The inside lumen allows the insertion of other optional instruments or connecting elements such as ablation wires or optical fibres. In parallel to the long axis of each segment, and as shown in more detail in FIGS. 3 and 4, three channels each with a diameter of approximately 250 micrometers are incorporated. As shown in FIG. 4, two of these channels 34 and 36 are tendon guide channels formed in the cantilevered rings and extending parallel to the long axis of each segment, and into which guide tendons in the form of fluorocarbon string pass, to allow for manipulation of the catheter tip. The third channel 32 forms a backbone channel that runs within the backbone portion 22 of the segment and contains a carbon fibre rod, that allows for increased flexibility of the continuum manipulator. The guide channels 34 and 36 are arranged with respect to the backbone channel such that in Cartesian coordinates if the z-axis was co-axial with the carbon fibre rod, and the x axis extended from the carbon fibre rod so as to bisect a line drawn between the tendon guide channels 34 and 36, lines drawn from the (centre of the) carbon fibre rod to each of the guide channels would be for example at an angle of 22.5 degrees to the x axis. In other embodiments the tendon channels may be positioned such that a greater or lesser angle up to 90 degrees may be formed, with the angle used then determining the range of sideways movement of the catheter tip, as shown in FIG. 5.

To create a catheter tip, plural of the segments 12 are stacked one on top of each other in such a way that the tendon channels are in alignment, such that the fluorocarbon string tendons may be fed therethrough, as well as the carbon fibre backbone. The number of segments in any embodiment can vary depending on the application, to create either a shorter, or a longer, more manoeuvrable catheter tip. In this respect, note that each segment as described previously may bend up to, for example, 38 degrees, and hence the more segments that are included in a catheter tip, the greater the degree of bending of the whole continuum manipulator. The carbon fibre rod is used as a backbone through channel 32 in each segment to improve mechanical performance, flexibility, and repeatability of the steering mechanism. As well as mechanical reinforcement, the carbon fibre rod minimises the hysteresis effect, and helps the structure to "bounce" back to the initial state when tendons are released. Repeatability of the amount of bending is an important parameter for the steering mechanism as it is important for perception of catheter position during any catheterisation procedure.

As noted, in order to allow for manipulation of the catheter tip, two fluorocarbon strings 34 and 36 are provided through the tendon channels in each segment. In one embodiment the fluorocarbon strings have a diameter of 0.14 mm each, and can apply a maximum force of 21.5 Newtons. Each string is bonded to the segment at the tip of the continuum manipulator by, for example, epoxy glue, such as BONDLOC. The tendons may then be actuated using a motorised actuator, or a manual catheter navigation knob mechanism.

In order to manufacture the continuum manipulator in the form of the catheter tip of the present embodiment each individual segment 12 is manufactured, and then constructed by stacking one on top of the other about the carbon fibre backbone. For prototyping purposes, the present embodiment was produced using rapid prototyping techniques, using Prefactory Aureus machinery, available from EnvisionTec, of Gladbeck, Germany. The Aureus rapid prototyping machine employs a stereo lithography technique to cure photoreactive acrylate polymers layer by layer by emission of UV light reflected from a DLP module. The photoreactive acrylate polymer is a non-conductive MR compatible polymer which makes it suitable for this application. Once each segment has been produced, they can then be assembled in the number required for the application along the carbon fibre backbone, and the guide tendons inserted in to the tendon channels.

In use the catheter tip can be steered by virtue of the guide tendons 34 and 36 in the tendon channels. This is illustrated in more detail in FIGS. 4 and 5, and in particular FIG. 5 shows the catheter tip in a Cartesian co-ordinate system in which the Z axis is parallel to the segment and passes through the backbone channel, such that the carbon fibre rod passes through the channel located at the reference point and forms the flexible backbone of the continuum manipulator. The two tendon channels are located opposite the backbone and allow the segment to bend in the XZ plane (both tendons pulled) or to divert left and right from the XZ plane by an angle of for example up to 22.5 degrees in either direction (left or right tendon pulled, respectively). Different combinations of both tendon displacements result in bending in planes with any desired angle between these two extreme positions. For example, an equal actuation or displacement of both tendons would cause a bending along the carbon fibre rod and reference line.

The use of two tendons in the configuration of the first embodiment improves the manoeuvrability of the catheter tip, and increases the degrees of freedom. In particular, the provided steering mechanism is capable of navigating the catheter tip in a three dimensional space, instead of a two dimensional plane as is the case for traditional catheters. This steering mechanism therefore allows the surgeon to position the tip more accurately, and moreover, when applying tension to the guide tendons such that the catheter tip bends, the lateral stiffness of the catheter is increased, such that the surgeon can use the catheter to apply more force from the side of the catheter, if required. Thus, provision of the guide tendons 34 and 36 provides for steerability of the catheter tip in two degrees of freedom as well as providing a mechanism to increase the stiffness of the catheter, when the catheter is bent. In this respect, bending of the catheter by applying a force to the guide tendons increases the stiffness of the catheter tip.

One advantageous element of the present embodiment is the use of the carbon fibre rod 32 as a backbone for the continuum manipulator. The carbon fibre rod helps reduce hysteresis, by helping to ensure that the continuum manipulator returns to its original unbent position when the steering force on the guide tendons is released. FIG. 6 illustrates the change in position of the tip of the continuum manipulator forming the catheter tip 10 across 13 different positions. Here, the guide tendons were tightened at 1 mm intervals and scanned 13 times, to produce overlaid photographs shown on the left of the figure. As the guide tendons were tightened the position of the catheter tip was measured, as shown by the "forward" positions in the graph to the right of the figure. The catheter tendons were then released by 1 mm intervals and scanned again, with the position of the catheter tip then being measured again as shown by the "reverse" plot in the graph of FIG. 6. As will be seen, a small hysteresis effect is observed in the catheter trajectory when it returns back to the initial position, and it is thought that this is caused by three factors, being the unavoidable friction between the tendons and the guide channels, the tendon extension, and friction between the catheter and the scanner surface. In this respect, the fluorocarbon string used in the present embodiment benefits from low friction and high strength, but does, for a small diameter, result in some extension under force. In other embodiments other materials may be used for the control tendons for example, nitinol string or wire. In practice, friction due to the scanner surface used in the measurement would not occur.

Figure 7:
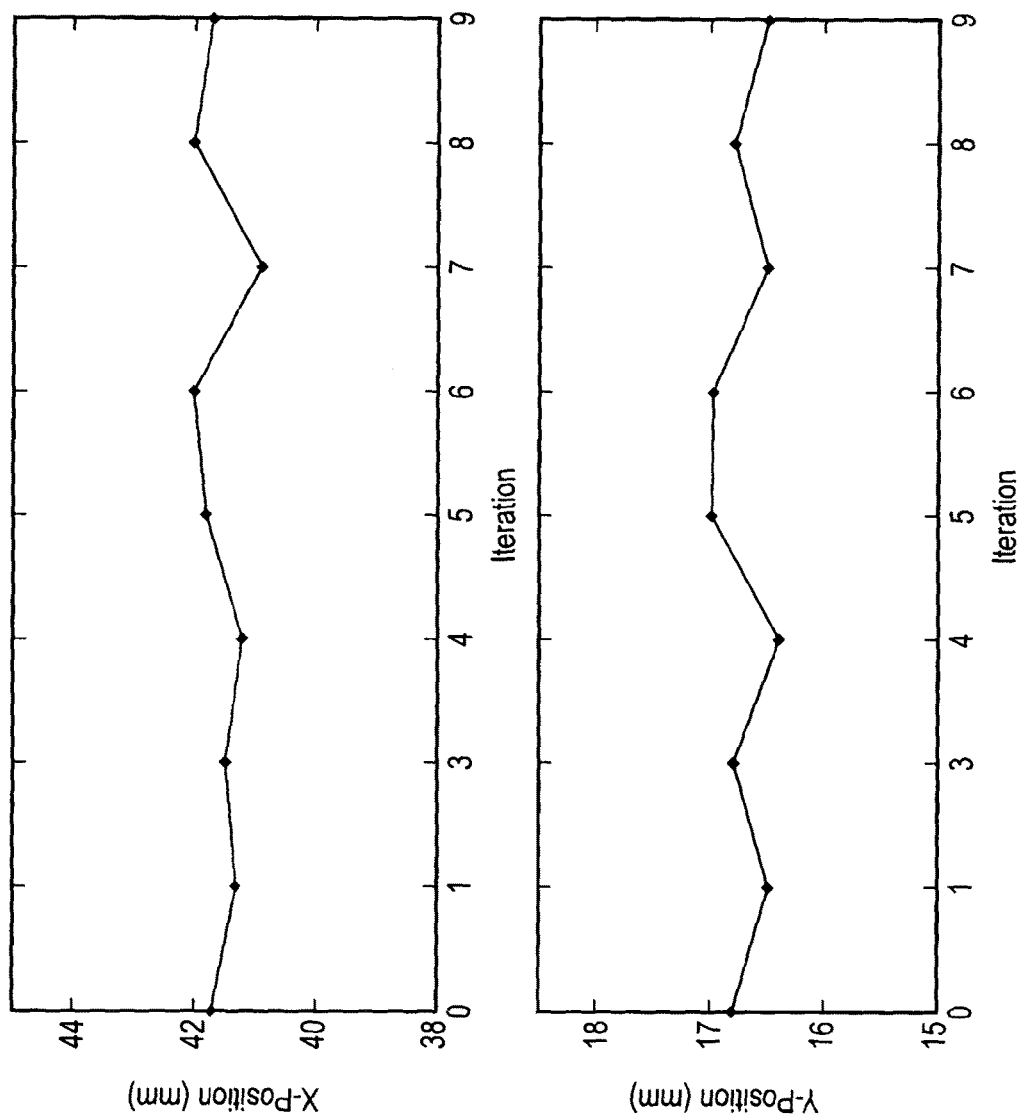
FIG. 7 is a pair of graphs illustrating the position of the end of the continuum manipulator over repeated iterations of movement.
Figure 10:
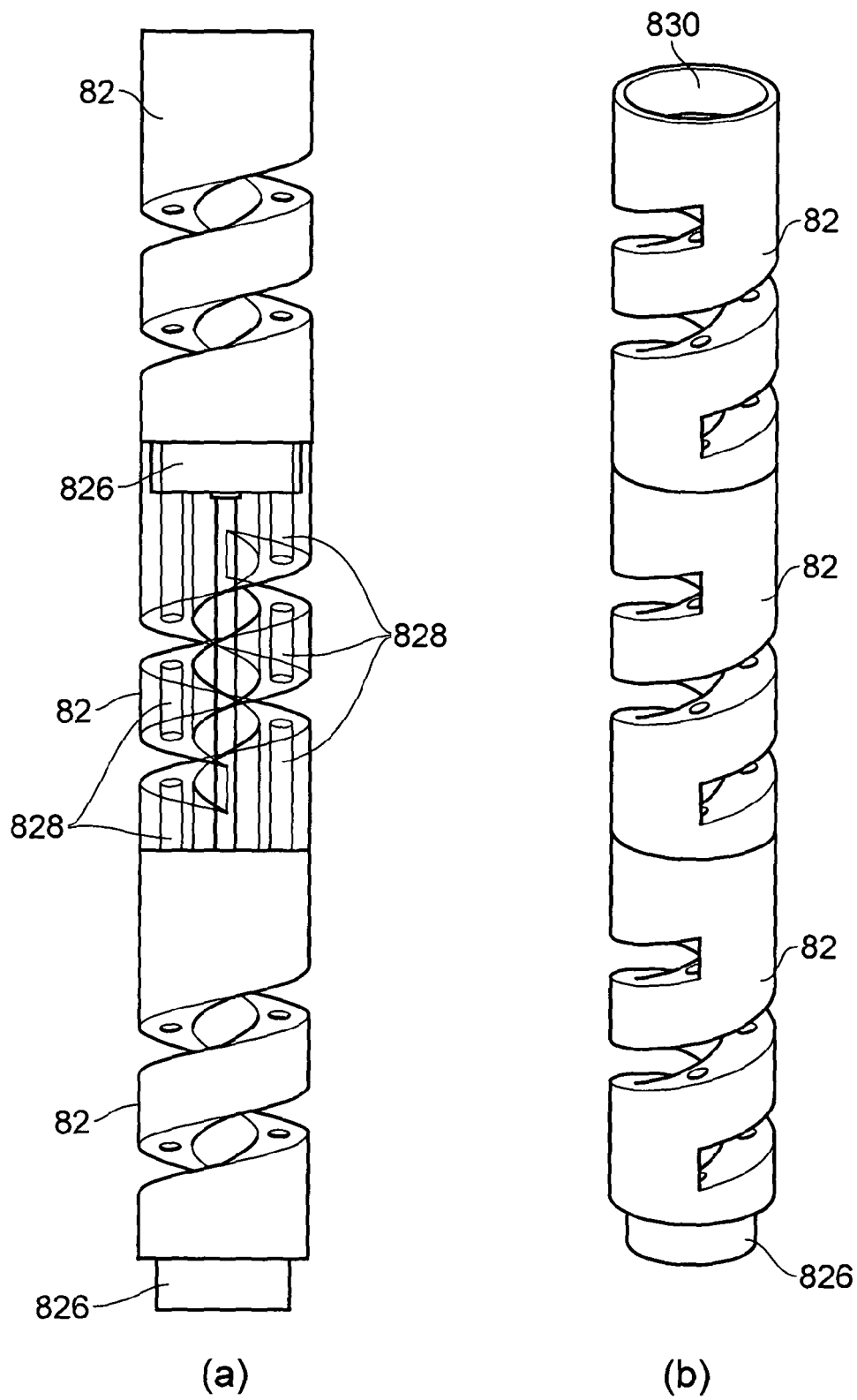
FIG. 10a is a side on partial cross-section of part of the continuum manipulator of the second embodiment.
FIG. 10b is a perspective view of part of the continuum manipulator of the second embodiment.
Figure 11:
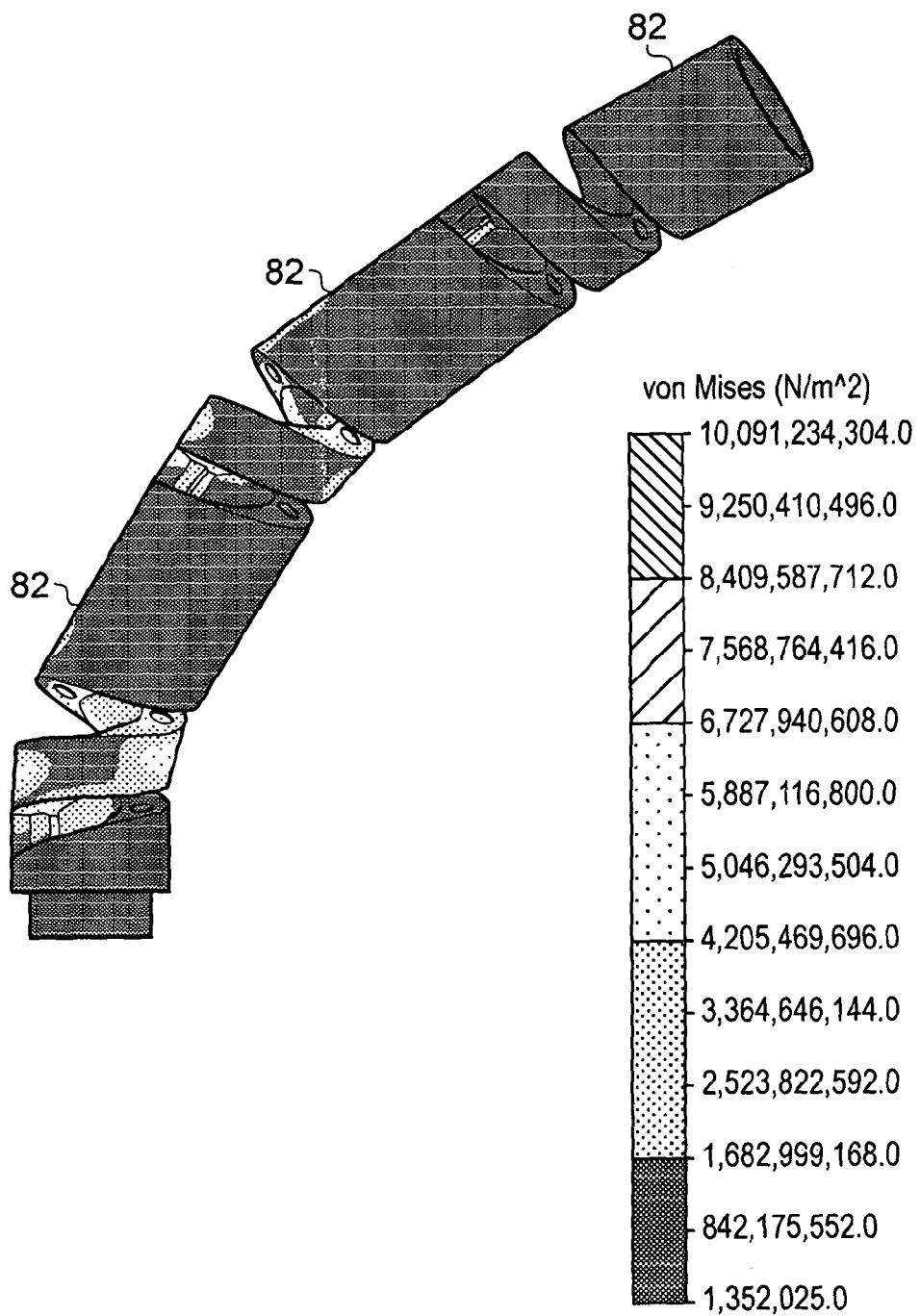
FIG. 11 is a drawing illustrating the bending of the continuum manipulator of the second embodiment.

In addition, FIG. 7 illustrates the results of tests of repeated bending of the catheter tip. In this respect, to obtain the results of FIG. 7 the catheter tendons were displaced by up to 6 mm, and the position of the catheter tip was then recorded. The tendons are then released allowing the catheter to return to the initial position, and then this was repeated for nine iterations. The X and Y positions of the catheter tip after each iteration are shown in the graphs of FIG. 7, for which it can be calculated that the standard deviation of final tip position in the X and Y axes is 0.4 mm and 0.2 mm respectively.

In variations of the first embodiment different materials may be used for the backbone, other than carbon fibre. The important feature of the backbone is that it has elastomeric properties, which allow the backbone to spring back repeatedly to its original shape, carrying the continuum with it. Preferably, to allow for MR compatibility in catheter applications the backbone should also be formed from a non-conductive material, so as to be MRI compatible. Example materials may be polyethylene, PVC, neoprene, polyesters, or silicone or fluorosilicone elastomers.

A second embodiment of the invention will now be described with respect to FIGS. 8 to 11.

FIG. 8 shows two photographs of a continuum manipulator in the form of a steerable catheter tip according to the second embodiment of the invention. In particular, the catheter tip 80 is again formed from individual stacked segments 82, as shown in more detail in FIG. 9. The individual stacked segments 82 stack one on top of each other using a male and female mating arrangement, and the catheter tip can bend in any direction from the straight position shown in the photograph on the left hand side of FIG. 8, to a bent configuration shown in the photograph on the right hand side of FIG. 8.

As mentioned, FIG. 9 shows respectively top and bottom perspective views of a segment 82 of the catheter tip 80. Each segment 82 is generally cylindrical in shape, but arranged in a helical configuration. In particular, each segment 82 is arranged as a hollow cylinder with a lumen channel 830 running along the centre thereof. One end of the segment 82 forms a female connecting ring 822 and at the opposite end of the cylinder structure 82 is a circular male mating projection 826, which is arranged to fit inside the female mating ring 822 of another of the segments 82, when stacked one on top of the other. The cylindrical structure of each segment 82 has cut in the walls therein a helical segment, such that walls of each segment form a helical structure 824. In addition, formed within the helical walls of the segment 822 running parallel to the long axis of each segment are a plurality of tendon guide channels 828. Each tendon guide channel is, in this embodiment, approximately 250 microns in diameter. As shown, each tendon guide channel 828 runs from within the wall of the circular male mating projection 826, through the wall of the segment forming the helical part. However, the tendon guide channels are not formed in the wall of the female mating ring, which is much thinner than the wall of the helical part of the segment 82. In particular the upper surface of female mating ring 82 is arranged in use to abut against surface 832, located adjacent to and coaxially with male mating projection 826.

In this embodiment, there are four tendon guide channels 828, which are located approximately 90 degrees from each other around the circumference of the segment. The lumen 830 running through the centre of the segment is of approximately 1.3 mm in diameter, and is provided to allow the insertion of medicine delivery tubes, or can be used as a channel for electrical wires, optical fibres, or the like.

The primary advantage of the segment 82 of the second embodiment is that the helical arrangement of each segment allows each segment to freely bend away from the longitudinal axis of the segment in any direction. With four guide tendons, multi directional controlled bending can be achieved.

FIGS. 10a and b illustrate how multiple segments 82 can be stacked one on top of each other with the respective tendon guide channels of each in alignment, to produce a continuum manipulator to form a catheter tip. FIG. 10(a) in particular illustrates how the male and female mating rings 826 and 822 interact, where it can be seen that the male mating projection 826 of a first segment 82 is inserted into the female mating ring 822 of another segment 82 positioned lower than it in the continuum, and abutting surface 832 abuts against the upper surface of the female mating ring 822. The tendon guide channels 828 are shown extending within the walls of the middle segment shown in crosssection and it can be seen how they end below the upper edge of the female mating ring, with the female mating ring then extending axially upwards beyond the ends of the tendon guide holes. Conversely, as shown in the right hand figure of FIG. 9, the male mating ring 826 has the tendon guide channels formed therein. As a consequence, when two segments are placed together and the guide channels aligned, a continuous guide channel is formed from the male mating ring of one segment into the body of the mating segment, beneath the female mating ring 822 thereof.

The helical arrangement of the second embodiment provides significant advantages over the first embodiment. Firstly, as noted, each individual segment can bend in any direction away from the longitudinal axis of the segment, and hence by providing four tendon guide wires located approximately 90 degrees apart, each segment, and hence the continuum manipulator formed from each segment as a whole, can be caused to bend in any direction away from the longitudinal axis of the continuum manipulator when no force is applied. Whilst four such tendon guide wires are preferable, in other embodiments fewer or more guide wires may be used, although the minimum to achieve control in any direction is three wires, arranged approximately 120 degrees apart.

In addition, a further advantage is obtained that if all four tendons are equally pulled, then the length of the catheter tip can be made to reduce, as the individual segments compress upon each other like a spring. This not only reduces the length of the catheter tip, but also significantly changes the stiffness of the continuum. This can be important, as increasing the stiffness of the catheter tip can allow a surgeon to apply more force with the catheter tip for example in ablation procedures. In addition, by careful control of the tendons both stiffness of the catheter tip can be increased, as well as allowing for bending of the tip in any direction. This is achieved by, for example, applying the same force to all four guide tendons to compress the tip and stiffen it, and then applying additional force to those guide tendons, being a subset of all the tendons, required to cause the tip to bend in a required direction.

Another significant feature of the arrangement is that the tendon channels are integrated into the helical shape of each segment, such that the guide tendons pass through the inside of each segment, rather than along the outside of the catheter tip. This prevents twisting of the catheter tip, and allows improved torqueability of the tip. Specifically, by placing the guide tendons inside the channels, the whole continuum structure is made to conform to the channel, and hence twisting of the tip along its length is substantially prevented.

As in the first embodiment, the tendon guide wires may be formed from fluorocarbon string or nitinol wire, which is MRI compatible. Likewise, the segments 82 may be formed using a rapid prototyping machine using acrylate polymer, again as in the first embodiment, and which is also MRI compatible.

In use, the catheter tip of the second embodiment is steered and/or stiffened, by manipulation of the tendon guide wires, either by robot, or by hand. In order to bend in a particular direction the tendon guide wires nearest to the intended direction of bend are pulled, so as to have a force applied thereto. As mentioned, combined stiffening and bending of the continuum manipulator forming the catheter tip can be obtained by applying force to all the tendon guide wires to stiffen the continuum structure, and then varying the force on particular of the guide wires, depending on the direction of bend required. For example, applying more force on one of the wires will cause the structure to bend in the direction of the tendon channel containing that wire. On the other hand, a bend in the opposite direction may be obtained by releasing some of the force applied to the same guide wire, although with the result that the stiffness of the continuum would decrease.

In order to have a specific curvature profile for specific applications of the second embodiment the helical pitch can be altered from segment to segment up the continuum, so that the degree of individual bending achieved from different segments in the stack is different for the same applied force, when tested individually. For example, a helical pitch which has a smaller gap will result in less bending of a segment, whereas a helical pitch with a larger gap will result in more bending for the same applied force. To try and obtain a continuum manipulator with specific bending profile along its length for example those segments at the bottom of the stack may have a helical pitch that results in a "stiffer" segment (i.e. bends less for the same applied force), whereas those segments at the top of the stack should have a helical pitch that results in a "looser" segment, i.e. that bends more for the same applied force. Preferably, the stiffness of each segment should decrease from the bottom of the stack to the top of the stack that forms the catheter tip, to try and obtain uniform bending along the length of the continuum stack. In other embodiments, however, different combinations of segments of different stiffness i.e. of different helical pitch and/or helical gap size may be used along the length of the stack, depending on the bending profile required. In this respect, a desired bending profile along the stack can be specifically obtained by arrangement of segments of different stiffness along the stack.

Figure 12:
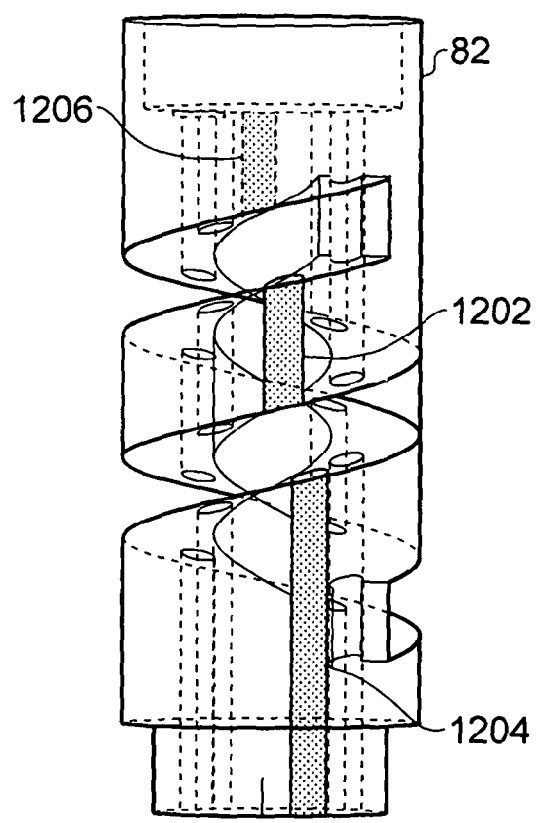
FIG. 12 is a cross-sectional view of a segment of a continuum manipulator according to a third embodiment.

A third embodiment of the invention will now be briefly discussed with respect to FIG. 12. The third embodiment is similar to the second embodiment discussed above, but adds the variation that, in addition to the four aligned tendon channels 828 in a particular segment 82, an additional tendon channel formed from non-aligned individual channels 1206, 1202, and 1204 is provided. An additional tendon formed from fluorocarbon string is provided in the non-aligned channels, which when pulled causes the three channels 1202, 1204 and 1206 to align, thus twisting the segment about its long axis. This provides a mechanism to twist at least one segment, and hence other segments above it in the stack in a controlled manner, to obtain a twist movement at the catheter tip.

In use, segments containing the twisting guide channel may be stacked one on top of the other as previously described. To ensure continuity of the twisting tendon from one segment to the next the upper twisting guide channel 1206 of one segment should be aligned in the stack with the lower twisting guide channel 1204.

With such an arrangement the catheter tip may be caused to bend in any direction by virtue of the four guide tendons, and may also be caused to rotate about its long axis by applying force to the twisting control tendon within the twisting guide channels.

Figure 13:
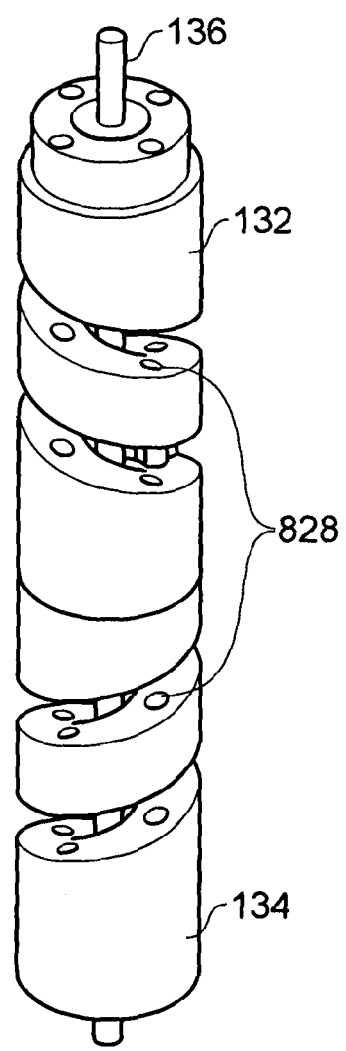
FIG. 13 is a perspective view of part of a continuum manipulator according to a fourth embodiment.
Figure 15:
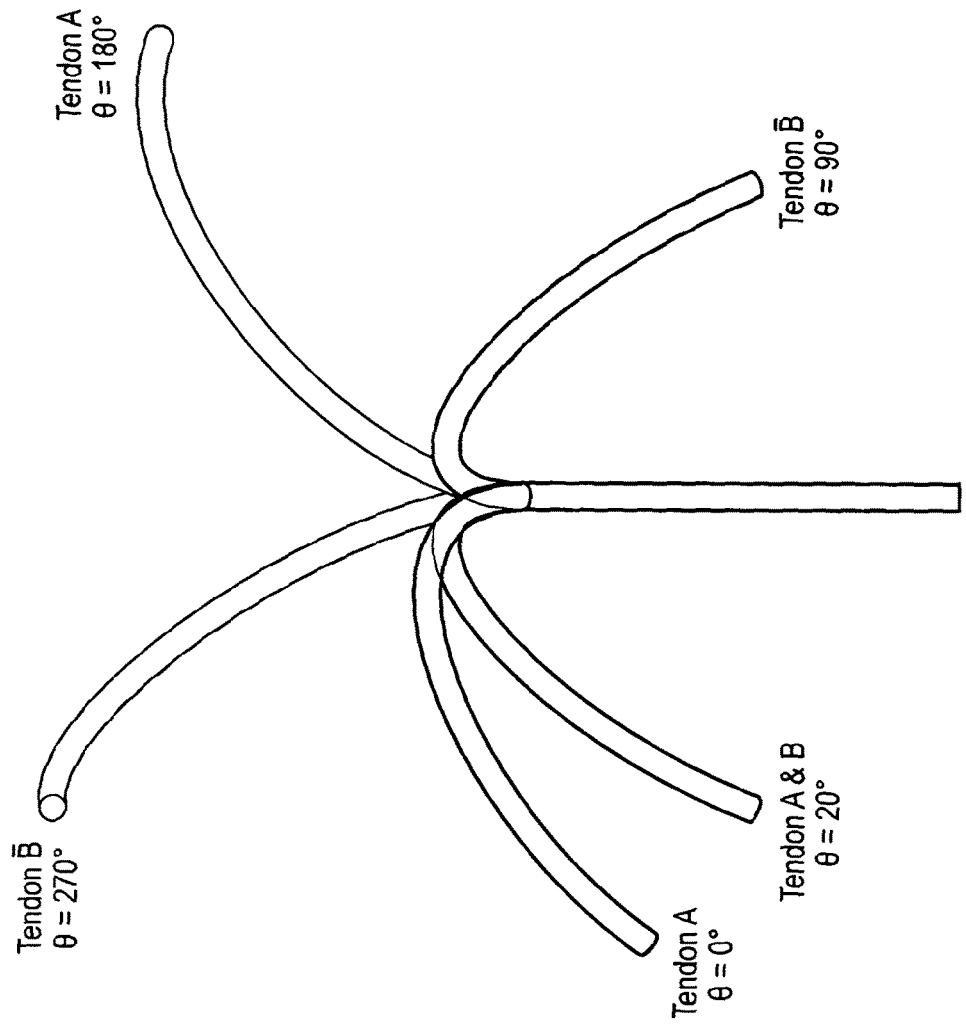
FIG. 15 is a perspective drawing illustrating the bending of the continuum manipulator of any of the second to fourth embodiments when particular control tendons are activated.
Figure 14:
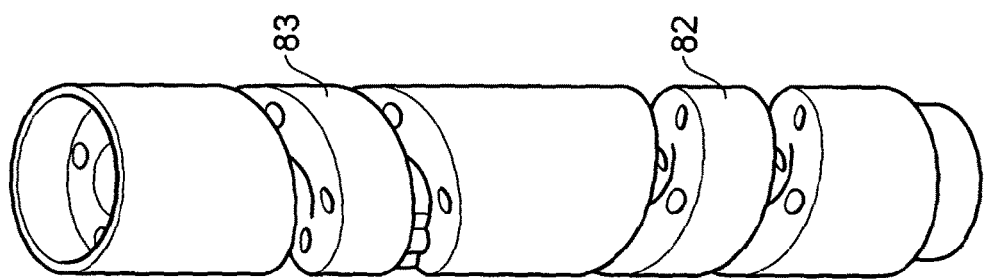
FIG. 14 is a is a perspective view of part of a continuum manipulator of another version of the fourth embodiment.

A fourth embodiment of the invention is shown in two variants in FIGS. 13 and 14. This is again based on the second embodiment of the invention described previously, but with two changes.

The first change is that in order to avoid unwanted twisting or rotation of the continuum stack when force is applied to the guide wires different segments and of the continuum stack are formed with the helical portions thereof extending in opposite rotational directions. For example, as shown in the variant of FIG. 13 the helix of the helical portion of segment 132 extends in a clockwise direction from the bottom of the segment to the top as shown in the drawing. Conversely, the helix of the helical portion of segment 134 extends in a counter-clockwise direction from the bottom of the segment to the top as shown in the drawing. The same is shown in the variant shown in FIG. 14, which in all other respects is identical to the second embodiment, but where segments 82 and 83 extend from the bottom of each segment in counter-clockwise and clockwise directions respectively. The net result of these different turning directions for the helices is that when a compression or bending force is applied to the guide tendons that at least partially compresses each segment as if it were a spring, the net rotation of the tip of the stack about the long axis of the stack should be substantially zero. This is because the individual small clockwise and counter-clockwise rotations of the individual segments that are otherwise made effectively cancel each other out.

To obtain this cancellation effect there should be substantially the same number of clockwise helix segments in the stack as there are counter-clockwise helix segments. In addition, although it is thought perhaps preferable for the clockwise and counter-clockwise segments to alternate along the stack, such that a clockwise segment is followed by a counter clockwise segment and so on along the stack, this is not essential, and the individual segments may be arranged along the stack in any order provided there are roughly equal numbers of each type of segment.

The second feature of the variant shown in FIG. 13 of this fourth embodiment different from the second embodiment is the inclusion of a carbon fibre backbone rod, running within the central lumen of the stack. As in the first embodiment, inclusion of a carbon fibre backbone increases the bendability of the stack, and in particular is thought to reduce hysteresis and improve repeatability of bending, in terms of the stack bending to the same point for the same force applied to the guide tendons. Location of the rod in the central lumen means that multiple smaller lumens (not shown) may be provided running adjacent to the rod through each segment, to allow for medicine delivery, optical fibres, or the like.

The embodiments described above relate generally to catheter tips. However, the continuum manipulator arrangements described may be applied on any scale, including significantly larger scales. For example, it is possible to envisage continuum manipulators of the type described with the control tendons being operated by robot being incorporated into robot explorers, such as for undersea or planetary surface exploration. Likewise, terrestrial applications may be found in the form of robot manipulators such as robot arms in factories, or as use as cranes in construction. The ability of the continuum manipulator of the second embodiment particularly to allow for controlled movement in any direction away from the long axis of the manipulator means that it is particularly suitable for many applications.

Various modifications may be made to the above described embodiments, whether by way of addition, substitution, or deletion, to provide further embodiments any and all of which are intended to be encompassed by the appended claims.

The invention claimed is:

1. A continuum manipulator comprising a plurality of segments arranged in a stack, the segments being deformable in a range of directions away from the long axis of the stack to allow the stack to bend in any of the range of directions away from the long axis thereof, wherein at least one of the segments comprises a helical portion wherein the wall of the segment extends helically around and in the direction of the long axis of the stack, the helical portion being able to deform in any direction away from the long axis, wherein a plurality of segments in the stack have helical portions, and wherein a first subset of one or more segments of the plurality of segments have helical portions that wind in a clockwise direction, and a second subset of one or more segments of the plurality of segments have helical portions that wind in a counter-clockwise direction.

2. The manipulator according to claim 1, further comprising:
a backbone channel running through each segment parallel to the long axis thereof and being arranged in the stack with the respective backbone channels in alignment, and
an elastomeric rod inserted into and running through the backbone channels of the segments.

3. The manipulator according to claim 1, wherein the segments further comprise at least one tendon guide channel formed therein substantially parallel to the long axis thereof, the manipulator further comprising a control tendon running through the guide channels and affixed to at least one of the segments to allow a bending or compression force to be applied to the stack when the control tendon is activated.

4. The manipulator according to claim 3, wherein the control tendons are formed from fluorocarbon string.

5. The manipulator according to claim 1, wherein the segments further comprise a lumen channel formed therein and extending parallel to the long axis thereof, the segments being arranged in the stack in alignment to provide a lumen channel running through the stack.

6. The manipulator according to claim 1, wherein the segment with the helical portion further comprises:
a mating projection, and a mating ring, the mating projection being located at an opposite end of the segment from the mating ring, the mating ring and mating projection being respectively sized such that the mating projection of one such segment is received within the mating ring of another such segment when such segments are arranged in the stack.

7. The manipulator according to claim 1, wherein the segments comprise at least three tendon guide channels formed therein substantially parallel to the long axis thereof, the manipulator further comprising respective control tendons running through the guide channels and affixed to at least one of the segments to allow a bending or compression force to be applied to the stack when one or more of the control tendons are activated.

8. The manipulator according to claim 1, wherein the helical portions are compressible to increase the stiffness of the stack.

9. The manipulator according to claim 1, wherein a majority of segments in the stack have helical portions.

10. The manipulator according to claim 1, wherein there are substantially equal numbers of segments in the stack with helical portions that wind clockwise and counter-clockwise.

11. The manipulator according to claim 1, wherein at least some of the segments further comprise a twist control tendon channel, the twist control tendon channel being formed within a segment from a plurality of twist control channels that extend parallel to the long axis of the segment but only along a respective part of the length of the segment, the channels being further laterally offset from one another, the arrangement further comprising a twist control tendon running through the twist control channels, and being such that when a force is applied to the twist control tendon the twist control channels are pulled into alignment, thereby at least partially rotating at least part of the segment.

12. The manipulator according to claim 1, wherein the manipulator is a steerable catheter tip.

13. The manipulator according to claim 12, wherein the diameter of the stack is 0.5 mm to 3 mm, and the length of each segment is in the range 1-100 mm.

14. The manipulator according to claim 12, wherein the catheter tip is made of magnetic resonance compatible materials.

15. The manipulator according to claim 12, wherein the segments are formed from acrylate polymer.

* * * * *